United States Patent
Weidner

Patent Number: 5,282,927
Date of Patent: Feb. 1, 1994

[54] CONCENTRATING EVAPORATOR

[76] Inventor: Mark Weidner, 2519 Nob Hill Pl. North, Seattle, Wash. 98109

[21] Appl. No.: 697,851

[22] Filed: May 9, 1991

[51] Int. Cl.$^5$ .......................... B01D 1/00; B01D 3/04
[52] U.S. Cl. ................... 159/147.1; 159/22; 159/27.1; 159/44; 202/160; 202/206; 202/237; 202/259; 203/2; 203/DIG. 2; 203/DIG. 18; 422/100; 422/101
[58] Field of Search ............. 159/22, 47.1, 44, 27.1, 159/DIG. 32; 196/119; 203/DIG. 2, 86, 1, 2, DIG. 18; 422/101, 100; 202/160, 206, 235, 237, 259, 262, 267.1

[56] References Cited

U.S. PATENT DOCUMENTS

| | | | |
|---|---|---|---|
| 2,476,477 | 7/1949 | Berg | 203/DIG. 2 |
| 2,573,807 | 11/1951 | Piros et al. | 203/DIG. 2 |
| 2,642,386 | 6/1953 | Piros | 203/DIG. 2 |
| 3,291,703 | 12/1966 | Dvonch et al. | 203/DIG. 2 |
| 3,395,083 | 7/1968 | Gilmont | 203/DIG. 2 |
| 3,416,999 | 12/1968 | Shepherd et al. | 422/101 |
| 3,578,567 | 5/1971 | Malvin et al. | 203/DIG. 2 |
| 3,718,544 | 2/1973 | Sims | 202/185.3 |
| 3,960,668 | 6/1976 | Rush | 202/185.1 |
| 4,006,062 | 2/1977 | Bhuchar et al. | 203/DIG. 2 |
| 4,313,786 | 2/1982 | Smith | 159/22 |
| 4,372,820 | 2/1983 | Naevestad | 202/242 |
| 4,492,951 | 1/1985 | Apothaker et al. | 203/DIG. 2 |
| 4,822,455 | 4/1989 | Olrik | 202/238 |
| 5,017,500 | 5/1991 | Langer | 203/DIG. 2 |
| 5,022,967 | 6/1991 | Stieg | 203/DIG. 2 |

FOREIGN PATENT DOCUMENTS

| | | | |
|---|---|---|---|
| 3601450 | 7/1987 | Fed. Rep. of Germany | 422/101 |
| 0411871 | 1/1974 | U.S.S.R. | 422/101 |
| 0558682 | 6/1977 | U.S.S.R. | 203/DIG. 2 |
| 0673311 | 7/1979 | U.S.S.R. | 205/DIG. 2 |

OTHER PUBLICATIONS

Gunther, Francis A., and Roger C. Blinn, *Analysis of Insecticides and Acaricides,* Interscience Publishers, Inc., New York, 1955, pp. 231-233.

*Primary Examiner*—Virginia Manoharan
*Attorney, Agent, or Firm*—Robert W. Beach

[57] ABSTRACT

The concentrate holding lower portion of a sample and concentrate holding vessel has a jacket for shielding such concentrate holding portion from heat sufficient to volatilize appreciable solvent therefrom when the vessel is subjected to sufficient heat for effecting evaporative concentration of solution in such vessel.

5 Claims, 1 Drawing Sheet

STEAM BATH
HEAT SOURCE

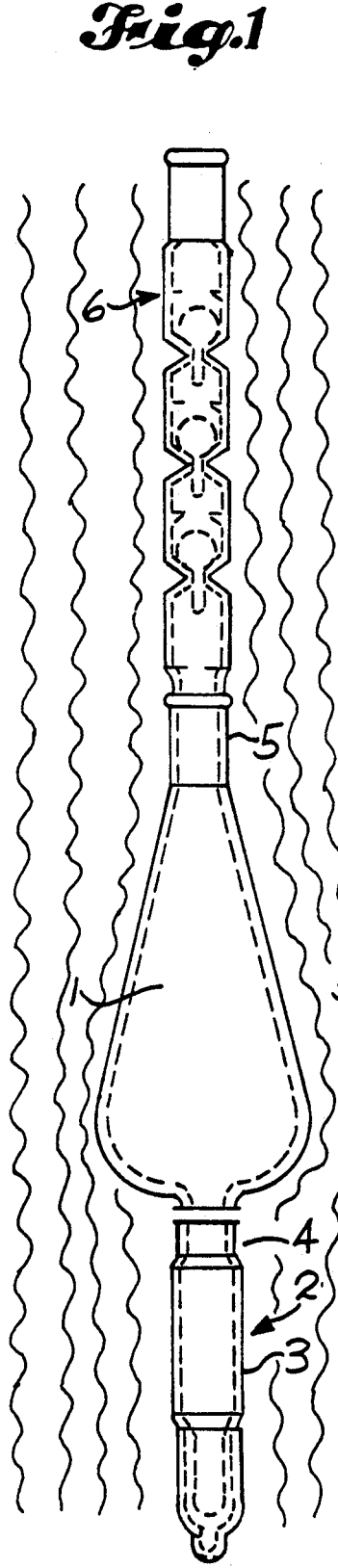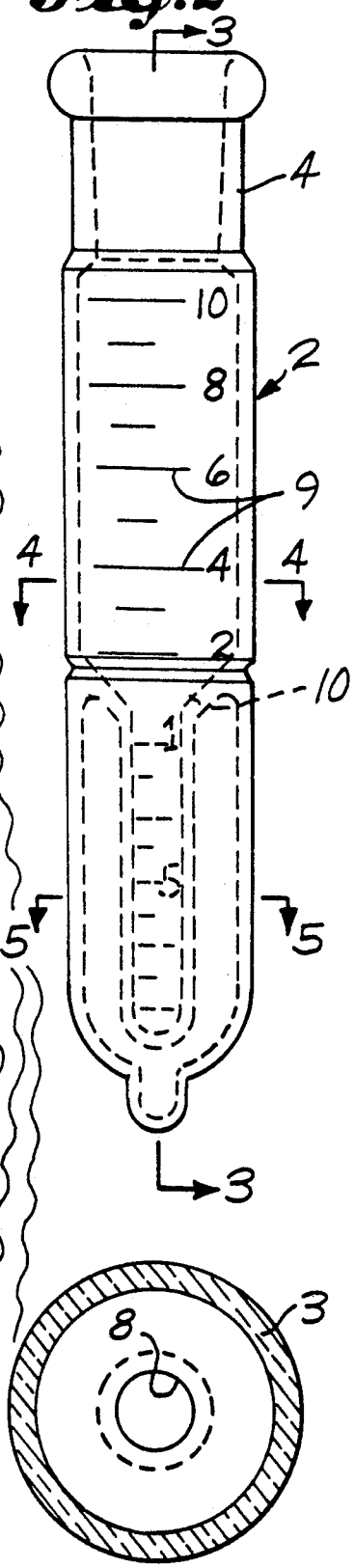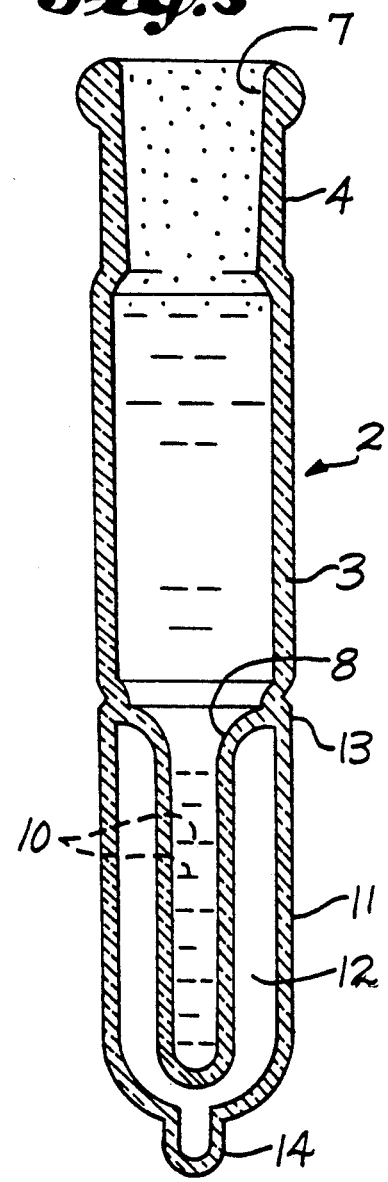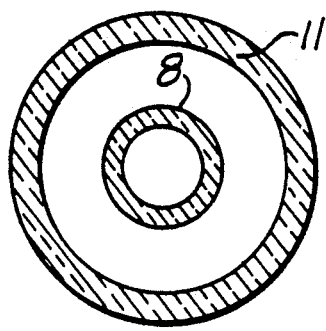
STEAM BATH HEAT SOURCE
Fig.1  Fig.2  Fig.3  Fig.4  Fig.5

CONCENTRATING EVAPORATOR

BACKGROUND OF THE INVENTION

1. Field of the Invention

This invention relates to evaporators for concentrating liquids to enable a small or trace amount of solute to be identified or processed.

2. Prior Art

Evaporative concentrators commonly used by commercial or testing laboratories have been of the columnar type usually composed of two or more sections including a principal evaporating section and a bottom sample-holding section. Such bottom section includes a concentrate holding lower chamber of a size much smaller in volume than the upper chamber of such lower sample-holding section. A collector and condensing-chimney section may be superimposed on the principal evaporating section.

The sections of the evaporative concentrator apparatus are tubular, preferably of circular cross section, and are usually made of Pyrex glass.

Such apparatus is commonly referred to as a Kuderna-Danish evaporative concentrator, an illustration and description of which are shown in the center unit of FIG. 14-3 on page 231 and described on pages 232 and 233 of the reference book *Analysis of Insecticides and Acaricides*, by Francis A. Gunther and Roger C. Blinn, Interscience Publishers, Inc., New York, copyright 1955. The description states that the apparatus is available from the Precision Distillation Apparatus Company, Santa Monica, Calif.

On page 232, it is stated that the concentrator is charged with the stripping solution to about the midpoint of the flask, and the unit is supported in a steam or boiling water bath in a good hood in such a way that the lower one-third of the flask is bathed in steam. When the receiver is nearly ∓dry", the unit is set aside to cool. Vapors within the unit then condense, to afford from 1 to 2 ml. of final solution within the receiver.

PROBLEM

In operation, the sample to be concentrated is placed in the sample-holding bottom section of the apparatus, the principal evaporating section is attached to the upper end of the sample-holding section and a collector and condensing-chimney is attached to the upper end of the principal evaporating section. The sample includes a solvent having a boiling point lower than that of water such as an organic solvent, for example, petroleum ether, ethyl ether or hexane.

The evaporator is subjected to an external heat source in the form of a heated atmosphere, usually steam emitted from a boiling water bath, to heat its exterior, which heat source is located externally of such evaporator and may be designated as an external heat source. Solvent is evaporated from the sample-holding section by heat from such heat source into the principal evaporating section and the vapor continues on up through the collector and condensing-chimney section.

A representative size of sample to be concentrated is 100 milliliters and it is usually desired to evaporate 99 milliliters of the sample solvent so that the resulting concentrate containing the solute will be approximately 1 milliliter.

The time required to reduce the volume of the sample from approximately 100 milliliters to approximately 1 milliliter will vary to some extent depending upon the type of solvent used and the temperature of the heating medium employed to heat the evaporator. Customarily, a number of samples are being concentrated in a number of evaporators at the same time in the same laboratory room, and it is difficult for a laboratory technician to remove each evaporator from the heated atmosphere or to remove the heated atmosphere from each evaporator at precisely the required time to prevent the sample from being concentrated too much, or even to prevent substantially all of the solvent being evaporated.

SUMMARY OF THE INVENTION

The principal object of the present invention is to effect termination of the evaporation in an evaporator automatically and without requiring the supervision of a laboratory technician when a desired set of conditions has been reached.

It is also an object to effect such termination with precision to enable consistent results to be obtained irrespective of the operating conditions.

A further object is to provide an evaporator which will produce the foregoing results effectively and reliably.

Another object is to accomplish the desired results with evaporating apparatus that is simple and inexpensive.

An additional object is to enable the foregoing results to be obtained by following customary operating procedure, in general, without requiring special programming or manipulation.

The foregoing objects can be accomplished by shielding the concentrate-holding chamber of the sample-holding section of the evaporator from heating atmosphere so as to prevent evaporation of solvent directly from such concentrate-holding lower chamber of the sample-holding vessel section.

BRIEF DESCRIPTION OF THE DRAWINGS

FIG. 1 is a side elevation of a columnar evaporator composed of three sections which incorporates the present invention.

FIG. 2 is an enlarged side elevation of the sample-holding bottom bottom sample-holding section of the evaporator on an enlarged scale.

FIG. 3 is a vertical longitudinal center section through the sample-holding section of the evaporator taken on line 3—3 of FIG. 2.

FIG. 4 is a horizontal transverse section through the upper chamber of the sample-holding section of the evaporator taken on line 4—4 of FIG. 2.

FIG. 5 is a horizontal transverse section through the sample-holding chamber of the concentrate-holding lower section of the evaporator taken on line 5—5 of FIG. 2.

DETAILED DESCRIPTION

A representative prior art evaporator in which the present invention has been incorporated is shown in the drawings as including three Pyrex glass sections assembled in columnar relationship. The center section 1 is the principal evaporator into which vapors rise from a sample-holding section 2 which forms a vessel for holding a solution test sample to be concentrated by evaporating solvent from it. The upper chamber 3 of such sample-holding section which is of larger diameter than the lower chamber holds a principal part of the test sample. The upper end of such sample-holding section 2 has a neck 4 that receives a neck projecting downwardly from the lower end of the principal evaporating chamber section 1. The upper end of such evaporating chamber section has a neck 5 for receiving a neck on the lower end of the collector and condensing-chimney section 6. The interfitting necks have complementally tapered ground glass surfaces to provide a vapor-tight joint.

As shown in FIGS. 2 and 3, the sample-holding section 2 is of circular cross-section and the cross-sectional area of the vaporizing upper chamber 3 of such section is greater than the area of the lower concentrate-holding chamber 8 of the section or vessel 2. The axial extent of the vaporizing upper chamber 3 is also considerably greater than the axial extent of the concentrate-holding lower chamber 8, so that the volume of the upper chamber is much greater than the volume of the concentrate-holding lower chamber. The volume of liquid in the sample-holding section can be indicated by graduations 9 in the upper chamber 3 and graduations 10 in the lower chamber 8 which are numbered to indicate milliliters. Preferably, the concentrate-holding lower chamber will hold approximately 1 milliliter and the vaporizing upper chamber 3 will hold about 9 milliliters, as indicated by the graduations.

An evaporator including the principal evaporating section 1, the sample-holding section 2 and a collecting and condensing chimney 6, as described thus far in detail, constitute an evaporator as customarily used heretofore.

The present invention involves shielding the concentrate-holding chamber 8 of the sample and concentrate holding vessel 2 from heat while the upper chamber 3 is unshielded so that even when the entire sample-holding vessel is subjected to hot fluid heat such as a steam bath heat source externally of the sample-holding vessel of the order of 212° F. (100° C.), the interior temperature of the concentrate-holding lower chamber 8 will be substantially cooler than the upper chamber 3 of the sample-holding vessel, namely, below the vaporization temperature of conventional solvents such as 95° to 140° F. (35° to 60° C.) While such shielding could be accomplished by providing various types of insulation for the concentrate holding lower chamber 8, the shielding can be accomplished most conveniently by enclosing such concentrate-holding chamber by a jacket 11 spaced from the concentrate-holding chamber to leave a substantial nonconducting space 12. This space may be evacuated to provide maximum heat shielding of the concentrate-holding chamber 8, but in most instances the shielding effect will be adequate if the space 12 is simply a dead air space.

Since the sample-holding section 2 of the evaporator is made of Pyrex glass, it is most convenient for the jacket 11 to be made of the same material. Such jacket could be simply the lower portion of a test tube of suitable size joined by a seal 13 to the wall of the sample-holding vessel section 2 adjacent to the upper end of the concentrate-holding chamber 8. The joint could be formed by joining the upper end of the jacket to the body of the sample-holding vessel section by suitable adhesive or the joint could be a fused joint.

In production the jacket 11 can be blown in place, in which case the joint 13 will be a fused joint. Preferably the jacket 11 with the concentrate-holding chamber 8 which it encloses as shown in FIG. 5 has the same cross-sectional size as the upper portion of the sample-holding vessel shown in FIG. 4 section 2. The lower portion of the jacket will be rounded and finished with a tip 14. The thickness of the jacket wall can be approximately the same thickness as the wall of the sample-holding vessel section 2.

A sample-holding vessel section 2 having a jacketed concentrate-holding lower chamber 8 and an unjacketed vaporizing upper chamber 3 will be used the same as a conventional sample-holding vessel in that a 10 milliliter solution sample can be poured through the neck 4 into the sample vessel section 2. Such vessel section could then be assembled with a principal evaporator section 1 and, if desired, a collector and condensing-chimney section 6, as shown in FIG. 1. The evaporator assembly is then subjected to a hot water or steam bath heat source which will heat the vaporizing upper chamber 3 of the sample-holding section and the principal evaporator section 1 so as to evaporate solvent for reducing the volume of the solution sample until such upper chamber is devoid of liquid. At that point the concentrate-holding lower chamber 8 will be substantially full of concentrated liquid constituting a predetermined residual volume of the solution sample and the evaporation in the sample-holding vessel section will terminate automatically because, by shielding only the concentrate-holding lower chamber of the sample-holding vessel section from heat from the heat source to a degree to maintain the interior of the concentrate-holding lower chamber at a temperature below the vaporization temperature of the solvent, the temperature of the concentrated liquid in the concentrate-holding lower chamber 8 will not be high enough to evaporate solvent from it, which will automatically limit the evaporation-effected reduction in volume of the solution sample in the sample-holding vessel section to a volume substantially equal to the volume of the concentrate-holding lower chamber of the sample-holding vessel section even while still subjecting the exterior of the sample-holding section 2 to heat from the heat source.

I claim:

1. In a concentrating evaporator including a sample-holding vessel for holding a sample containing solvent having a vaporizing upper chamber and a concentrate-holding lower chamber and further including a hot fluid heat source externally of the sample-holding vessel for heating the exterior of the sample-holding vessel, the improvement consisting essentially of the upper chamber of the sample-holding vessel being unshielded for enabling access of heat from said external heat source to said upper chamber for vaporizing solvent form the sample therein, and means located between the heat source and the concentrate-holding lower chamber for shielding only the concentrate-holding lower chamber of the sample-holding vessel from heat from such heat source for maintaining the temperature of the interior of the concentrate-holding lower chamber below the vaporization temperature of solvent in the sample in the concentrate-holding lower chamber so as to prevent vaporization of solvent in the concentrate-holding lower chamber, and thereby terminate vaporization of solvent form the sample-holding vessel when there is no remaining sample in the upper chamber.

2. In the concentrating evaporator defined in claim 1, the shielding means being heat-insulating means enclosing only the concentrate-holding lower chamber of the sample-holding vessel and leaving the upper chamber of the sample-holding vessel uninsulated.

3. In the concentrating evaporator defined in claim 2, the heat-insulating means including a jacket enclosing only the concentrate-holding lower chamber of the sample-holding vessel, the upper chamber of the sample-holding vessel being unjacketed.

4. In the concentrating evaporator defined in claim 3, the concentrate-holding lower chamber of the sample-holding vessel having a smaller cross-sectional area than the cross-sectional are of the upper chamber of the sample-holding vessel, and the concentrate-holding lower chamber of the sample-holding vessel in combination with the jacket enclosing it having a cross-sectional area substantially equal to the cross-sectional area of the unjacketed upper chamber of the sample-holding vessel.

5. In a process for evaporating solvent from a solution sample in a sample-holding vessel having a vaporizing upper chamber and a concentrate-holding lower chamber by subjecting the exterior of said vessel to a source of hot fluid heat externally of said vessel and thereby vaporizing solvent from said solution sample in said vaporizing upper chamber of said vessel, the improvement which consists essentially of automatically terminating vaporization of said solvent from said solution sample in said vessel at a predetermined residual volume of said solution sample by shielding only said concentrate-holding lower chamber of said vessel from heat from said heat source to a degree to maintain the interior of said concentrate-holding lower chamber at a temperature below the vaporization temperature of the solvent in said solution sample in said concentrate-holding lower chamber so as to prevent vaporization of solvent in said concentrate-holding lower chamber and thereby automatically limiting the evaporation-effected reduction in volume of said solution sample in said vessel to a volume substantially equal to the volume of said concentrate-holding lower chamber of said sample-holding vessel even while still subjecting the exterior of said vessel to heat from said heat source.

* * * * *

UNITED STATES PATENT AND TRADEMARK OFFICE
CERTIFICATE OF CORRECTION

PATENT NO. : 5,282,927
DATED : February 1, 1994
INVENTOR(S) : Mark Weidner

It is certified that error appears in the above-identified patent and that said Letters Patent is hereby corrected as shown below:

Claim 1: column 4, lines 51 and 62, cancel "form" and insert --from-- in each instance.

Claim 4: column 5, line 9, cancel "are" and insert --area--.

Signed and Sealed this

Twenty-eighth Day of June, 1994

Attest:

BRUCE LEHMAN

Attesting Officer     Commissioner of Patents and Trademarks